United States Patent
Whitehurst et al.

(10) Patent No.: US 7,610,103 B2
(45) Date of Patent: Oct. 27, 2009

(54) ELECTRODE ARRANGEMENT FOR NERVE STIMULATION AND METHODS OF TREATING DISORDERS

(75) Inventors: Todd Kevin Whitehurst, Santa Clarita, CA (US); Kirsten N. Jaax, Saugus, CA (US); Rafael Carbunaru, Studio City, CA (US); Janusz A. Kuzma, Parker, CO (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 507 days.

(21) Appl. No.: 11/311,502

(22) Filed: Dec. 19, 2005

(65) Prior Publication Data
US 2007/0142889 A1    Jun. 21, 2007

(51) Int. Cl.
*A61N 1/00*    (2006.01)

(52) U.S. Cl. ..................................... 607/118
(58) Field of Classification Search ............ 607/39, 607/41, 45, 46, 116, 118, 138, 117
See application file for complete search history.

(56) References Cited

U.S. PATENT DOCUMENTS

| | | | |
|---|---|---|---|
| 3,941,136 A | 3/1976 | Bucalo | |
| 4,542,753 A | 9/1985 | Brenman et al. | |
| 4,585,005 A | 4/1986 | Lue et al. | |
| 4,649,937 A * | 3/1987 | DeHaan et al. | 607/115 |
| 4,702,254 A | 10/1987 | Zabara | |
| 4,867,164 A | 9/1989 | Zabara | |
| 5,025,807 A | 6/1991 | Zabara | |
| 5,139,539 A | 8/1992 | Haynes, Jr. | |
| 5,239,540 A | 8/1993 | Rovira et al. | |
| 5,312,439 A | 5/1994 | Loeb | |
| 5,314,457 A | 5/1994 | Jeutter et al. | |
| 5,433,735 A | 7/1995 | Zanakis et al. | |
| 5,439,938 A | 8/1995 | Synder et al. | |
| 5,454,840 A | 10/1995 | Krakovsky et al. | |
| 5,571,118 A | 11/1996 | Boutos | |
| 5,741,319 A | 4/1998 | Woloszko et al. | |
| 5,775,331 A | 7/1998 | Raymond et al. | |

(Continued)

FOREIGN PATENT DOCUMENTS

WO    WO 98/37926    9/1998

(Continued)

OTHER PUBLICATIONS

U.S. Appl. No. 11/040,209, filed Jan. 20, 2005 by Colvin et al., for "Implantable Microstimulator with Plastic Housing and Methods of Manufacture and Use" (Not Published).

(Continued)

*Primary Examiner*—Carl H Layno
*Assistant Examiner*—Roland Dinga
(74) *Attorney, Agent, or Firm*—Darby & Darby P.C.; Patrick R. Turner (57) ABSTRACT

A stimulator arrangement for stimulating nerves or other tissue includes an electrode arrangement having a substrate and a plurality of electrodes disposed on the substrate. The substrate is configured and arranged to be in a curved state prior to implantation into the body and to flatten with exposure to the body after implantation. The stimulator arrangement may also include a stimulator unit coupled to the electrode arrangement. The stimulator unit may also be implantable.

14 Claims, 5 Drawing Sheets

U.S. PATENT DOCUMENTS

| | | | |
|---|---|---|---|
| 5,938,584 A * | 8/1999 | Ardito et al. | 600/38 |
| 6,051,017 A | 4/2000 | Loeb et al. | |
| 6,522,932 B1 | 2/2003 | Kuzma et al. | |
| 6,609,032 B1 | 8/2003 | Woods et al. | |
| 6,650,943 B1 | 11/2003 | Whitehurst et al. | |
| 6,735,474 B1 | 5/2004 | Loeb et al. | |
| 6,745,079 B2 * | 6/2004 | King | 607/117 |
| 6,788,975 B1 | 9/2004 | Whitehurst et al. | |
| 2003/0093139 A1 * | 5/2003 | Gibson et al. | 607/137 |
| 2004/0059392 A1 | 3/2004 | Parramon et al. | |
| 2004/0127942 A1 * | 7/2004 | Yomtov et al. | 607/3 |
| 2004/0186528 A1 * | 9/2004 | Ries et al. | 607/36 |
| 2004/0186543 A1 | 9/2004 | King et al. | |
| 2004/0220651 A1 * | 11/2004 | Kuzma et al. | 607/137 |

FOREIGN PATENT DOCUMENTS

| | | |
|---|---|---|
| WO | WO 98/43700 | 10/1998 |
| WO | WO 98/43701 | 10/1998 |
| WO | WO-2005107854 | 11/2005 |

OTHER PUBLICATIONS

U.S. Appl. No. 11/056,762, filed Feb. 11, 2005 by Tom He, for "An Implantable Microstimulator Having a Separate Battery Unit and Methods of Use Thereof" (Not Published).

U.S. Appl. No. 11/294,283, filed Dec. 5, 2005 by Whitehurst et al., for "Cuff Electrode Arrangement for Nerve Stimulation and Methods of Treating Disorders" (Not Published).

Supplementary Partial European Search Report, PCT/US2006061519, Jun. 3, 2009 (4 pgs.).

* cited by examiner

ELECTRODE ARRANGEMENT FOR NERVE STIMULATION AND METHODS OF TREATING DISORDERS

FIELD

The invention is directed to electrode arrays for nerve stimulation and treatment of disorders, devices containing the electrode arrays, and methods of manufacture and use. In addition, the invention is directed to implantable microstimulators with remote electrode arrays and treatment of disorders.

BACKGROUND

Recent estimates suggest that the number of U.S. men with erectile dysfunction may be near 10-20 million, and inclusion of individuals with partial erectile dysfunction increases the estimate to about 30 million. Electrical stimulation can be used to treat erectile dysfunction. The targets of electrical stimulation are the cavernous nerves. The cavernous nerves run bilaterally between the prostate and the rectum as they course from the sacral spinal cord to the corpora cavernosa in the penis. Near the rectum, the nerves form more of a plexus than a coherent nerve, and they are interlaced with small arteries and veins as well as fatty tissue. This collection of small nerve fibers, arteries, and veins can be referred to as the neurovascular bundle.

The neurovascular bundle containing the cavernous nerve fibers is exposed during a common procedure to remove the prostate, known as nerve-sparing radical prostatectomy. Following this procedure, approximately half of men are left impotent, and an additional number may not be able to achieve penetration.

The axons are unmyelinated and are very small in diameter which means that the stimulation threshold is relatively high. Also, the neurovascular bundle is adhered to the rectum, and separating it from the rectum may lead to damage of the cavernous nerve.

BRIEF SUMMARY

One embodiment is a stimulator arrangement for a nerve in a body of a patient. The stimulator arrangement includes an electrode arrangement having a substrate and a plurality of electrodes disposed on the substrate. The substrate is configured and arranged to be in a curved state prior to implantation into the body and to flatten with exposure to the body after implantation. The stimulator arrangement may also include a stimulator unit coupled to the electrode arrangement. The stimulator unit may also be implantable.

Another embodiment is a method of stimulating a nerve. The method includes disposing an electrode arrangement around at least a portion of a neurovascular bundle comprising the nerve and then at least partially flattening the electrode arrangement and neurovascular bundle. Electrical signals are provided to the electrodes of the electrode arrangement to stimulate the nerve.

Yet another embodiment is a nerve stimulator that includes a stimulator unit; an electrode arrangement for disposition adjacent the nerve; and a lead coupling the stimulator unit to the electrodes of the electrode arrangement. The electrode arrangement comprises a substrate and a plurality of electrodes disposed on the substrate. The substrate is configured and arranged to be in a curved state prior to implantation into the body and to flatten with exposure to the body after implantation.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The invention is directed to electrode arrays, as well as devices containing the electrode arrays, for nerve stimulation and treatment of disorders. In addition, the invention is directed to implantable stimulator devices, including microstimulators, with remote electrode arrays and treatment of disorders. For example, the electrode arrays can be used to stimulate the cavernous nerve to treat erectile dysfunction or other disorders. Stimulation of the cavernous nerve is described herein as an example of use of the inventive electrode arrays and devices; however, it will be recognized that the implantable electrode arrays and associated stimulator devices disclosed herein can be used to stimulate other nerves and tissues.

Electrode arrays can be disposed near or adjacent the cavernous nerve. The cavernous nerve, however, near the rectum is primarily a bundle of nerve fibers, veins, arteries, and fatty tissue. Thus, recruitment of nerve tissue for stimulation can be more difficult because of the intervening tissue. Moreover, in some instances, it is more convenient and/or advantageous to implant a stimulator unit, such as a microstimulator, elsewhere and then couple the stimulator unit via a lead, to electrodes disposed around or near the cavernous nerve. For example, implanting the stimulator unit elsewhere may be desirable so that the stimulator unit is less likely to be dislodged or otherwise moved from the original implanted position. In addition or alternatively, the stimulator unit may be implanted elsewhere to provide an easier site for removal of the stimulator unit if it should malfunction, cease functioning, or otherwise require replacement or removal. Finally, the stimulator unit may be implanted at a site where a rechargeable battery, if present, can be easily recharged.

Examples of suitable implantable stimulator devices, including microstimulators, that can be used or modified for use in stimulating the nerve include, but are not limited to, stimulator devices described in U.S. Pat. Nos. 5,139,539; 5,239,540; 5,312,439; 6,051,017; and 6,609,032; U.S. Patent Application Publication No. 2004/059392; U.S. patent application Ser. Nos. 11/040,209 and 11/056,762; and PCT Patent Applications Publication Nos. 98/37926; 98/43700; and 98/43701, all of which are incorporated herein by reference.

An implantable electrode array can be prepared that includes an electrode arrangement that can be positioned around the neurovascular bundle that contains the cavernous nerve. This electrode arrangement is formed so that, upon extended exposure to the body, the electrode arrangement at least partially flattens the neurovascular bundle so that the cavernous nerve fibers become positioned closer to the electrodes for stimulation. This can facilitate the recruitment of nerve tissue for stimulation by the electrodes. Optionally, the electrode arrangement can include posts that extend into the tissue from a substrate and contain electrodes to further position those electrodes close to the tissue to be stimulated.

Figure 1:
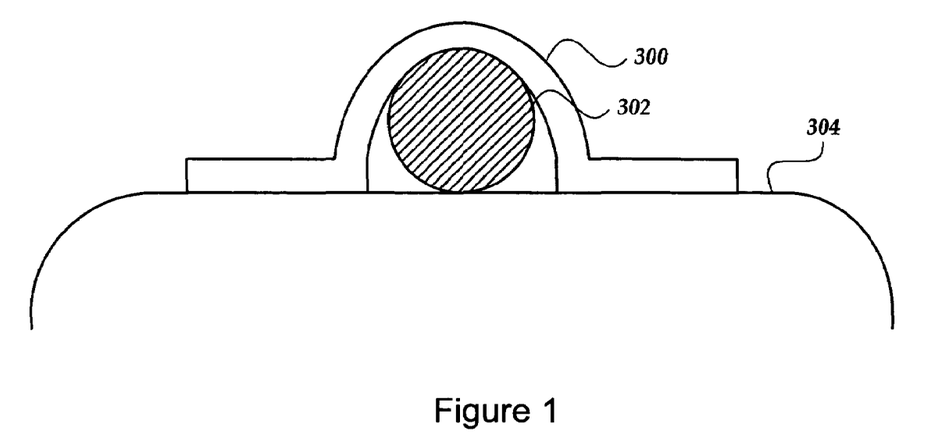
FIG. 1 is a schematic cross-sectional view of one embodiment of an electrode arrangement when the electrode arrangement is first implanted in the patient, according to the invention.
Figure 2:
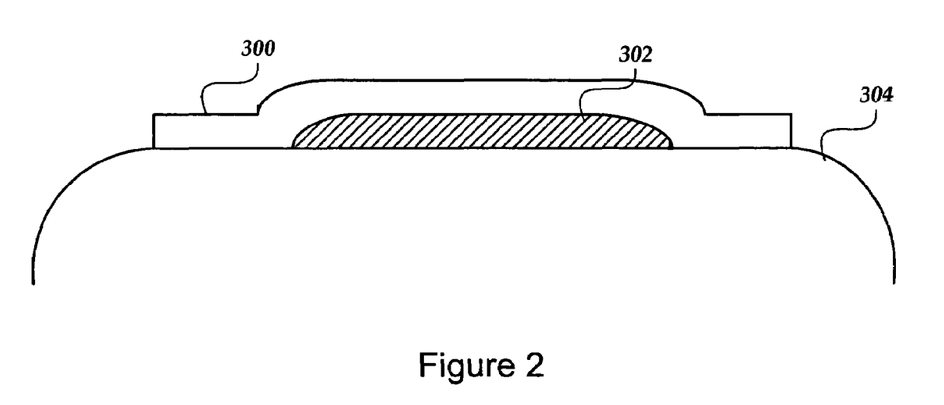
FIG. 2 is a schematic cross-sectional view of one embodiment of an electrode arrangement when the electrode arrangement has flattened after exposure to the body of the patient, according to the invention.

FIGS. 1 and 2 illustrate an electrode arrangement 300 in operation. Initially, upon implantation into the body, the electrode arrangement 300 is disposed around the nerve 302 (e.g., the neurovascular bundle) that is positioned over other tissue 304, as illustrated in FIG. 1. For example, the neurovascular bundle that includes the cavernous nerve is disposed over the rectum and the electrode arrangement can be disposed over the neurovascular bundle. The electrode arrangement 300 is initially in a curved state. Over time the electrode arrangement 300 flattens, as illustrated in FIG. 2, and flattens the nerve (or neurovascular bundle) against the other tissue. In the case of the neurovascular bundle containing the cavernous nerve this results in nerve fibers, particularly those close to the rectum wall, becoming closer to the electrode arrangement 300. This improves stimulation because the electric field generated by the electrodes decreases by the square of the distance between the electrodes and the nerve fiber. Thus, causing the nerve fibers to become closer to the electrode arrangement decreases the distance with a resulting increase in the electric field at the nerve fiber.

The flattening of the nerve or neurovascular bundle preferably does not substantially damage the nerve or cause necrosis in the nerve. For example, flattening of the neurovascular bundle containing the cavernous nerve can result in a rearrangement of the nerve fibers, veins, arteries, and fatty tissue in the bundle without substantially damaging these components.

Flattening of the electrode arrangement can be accomplished by a variety of methods. The flattening may be a relaxation or settling of the substrate induced, for example, by environmental conditions. As an example, the electrode arrangement can be prepared using a substrate material, such as a plastic, that initially retains a curved form. After implantation, the substrate material is heated to body temperature and the material becomes more flexible and flattens out under the influence of surrounding tissue. For example, the substrate material may be a plastic material that has a glass transition temperature that is greater than room temperature, but lower than or near body temperature. In another example, the substrate material may be a material that expands with hydration to form a flatter bottom surface against the tissue underlying the nerve and thereby flatten the nerve. In yet another example, the substrate material may be a material that changes shape when heated (e.g., nitinol changes phase upon heating and can be used as electrodes that alter shape upon heating.)

Figure 3:
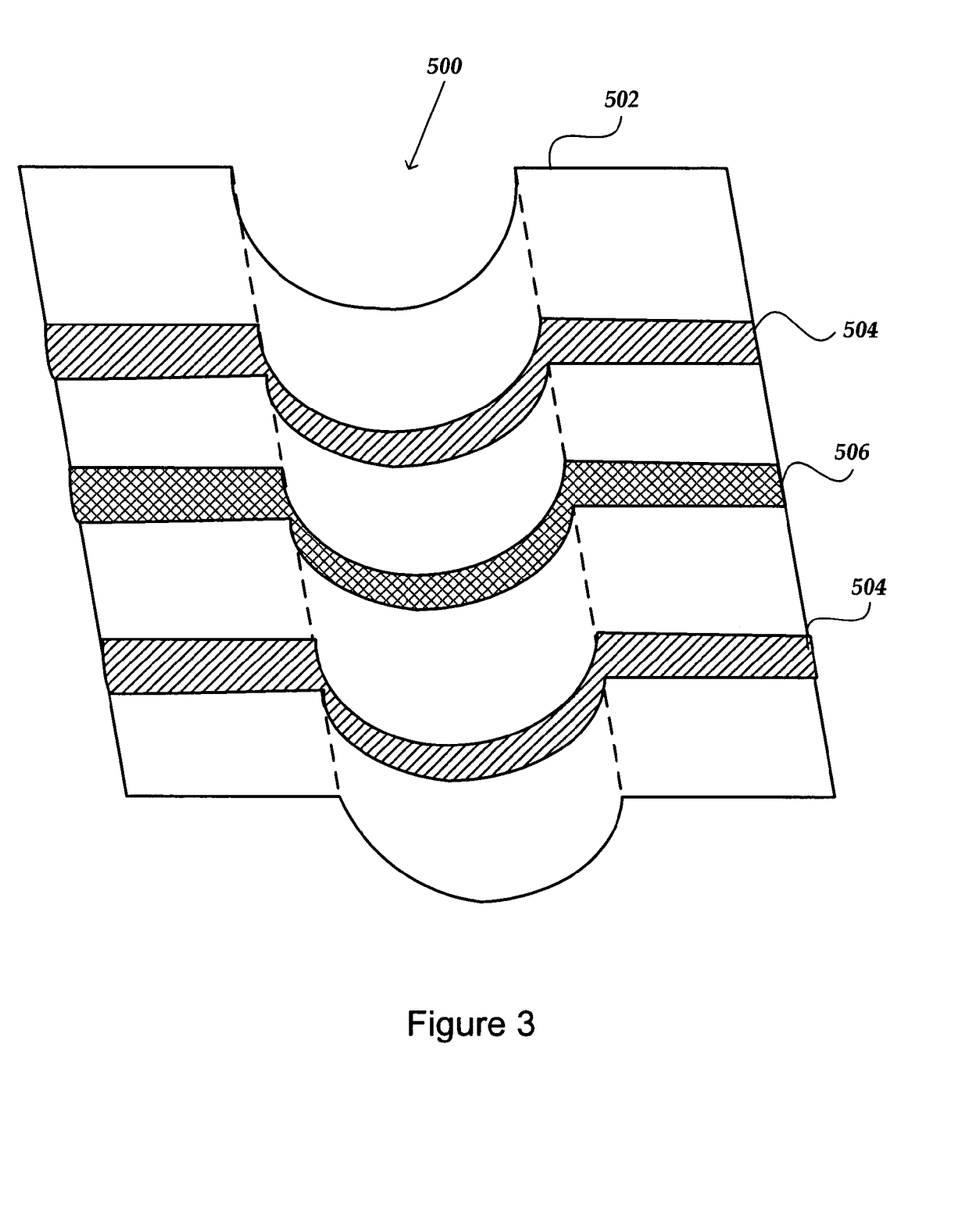
FIG. 3 is a schematic bottom view of one embodiment of an electrode arrangement, according to the invention.

FIG. 3 illustrates one embodiment of an electrode arrangement 500. The electrode arrangement 500 includes a substrate 502, one or more first electrodes 504, and one or more second electrodes 506. In the illustrated embodiment, there are two first electrodes and one second electrode; however, it will be understood that the electrode arrangement can include any number of first electrodes and any number of second electrodes. The electrodes 504, 506 are illustrated as strip electrodes disposed along the width of the substrate 502. It will be understood, however, that electrodes of any shape can be used including, for example, electrodes in the shape of discs, squares, rectangles, etc. as well as strip electrodes that are arranged lengthwise. The selection of which electrodes are anodes or cathodes and whether this selection is permanent or can be altered by the stimulator device may depend on the application and may be determined or established by a stimulator unit coupled to the electrodes.

Figure 4:
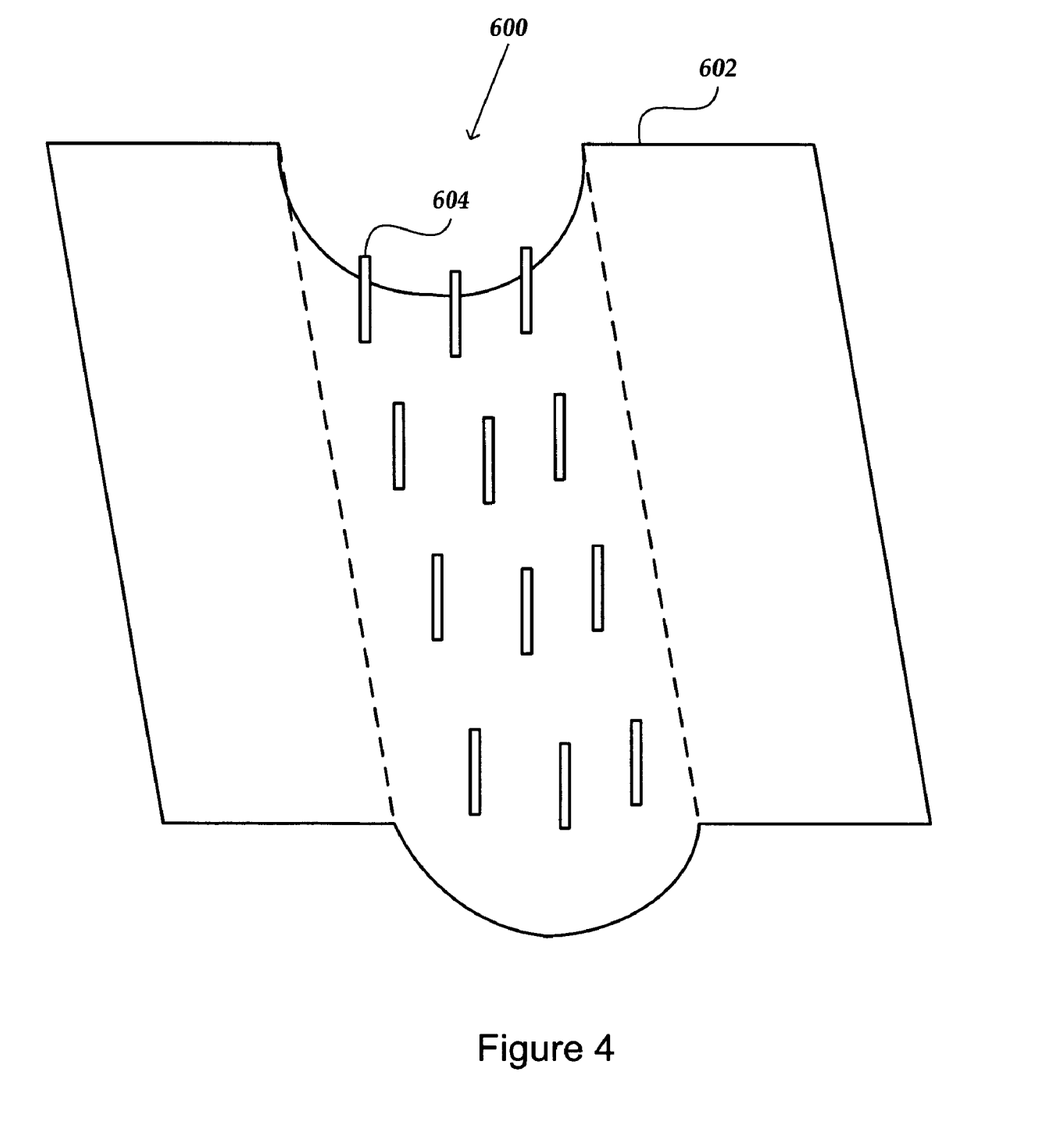
FIG. 4 is a schematic bottom view of another embodiment of an electrode arrangement, according to the invention.
Figure 5:
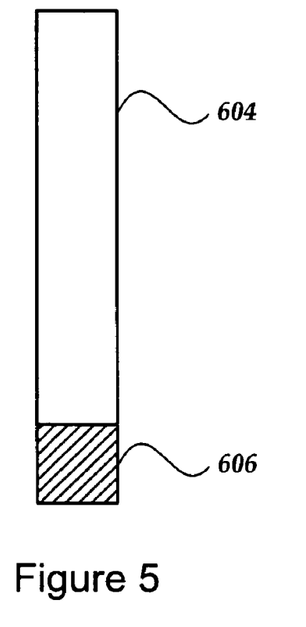
FIG. 5 is a schematic side view of one embodiment of an extension used in the electrode arrangement of FIG. 4, according to the invention.
Figure 6:
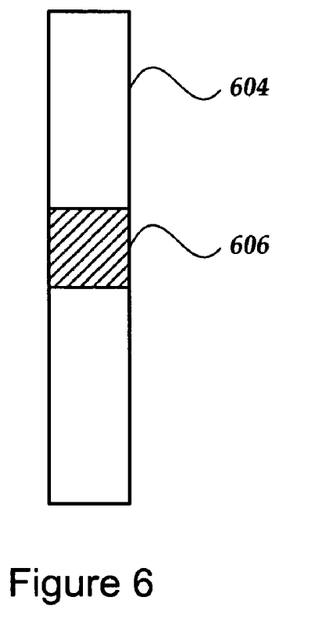
FIG. 6 is a schematic side view of another embodiment of an extension used in the electrode arrangement of FIG. 4, according to the invention.
Figure 7:
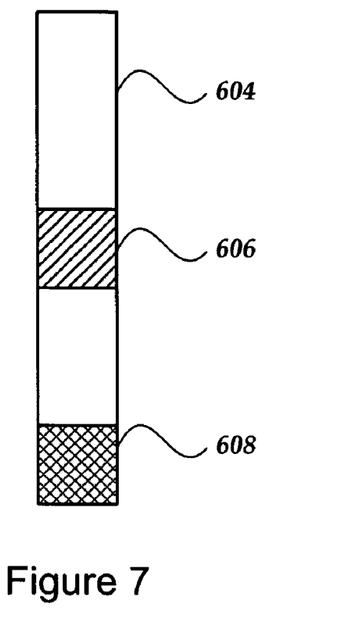
FIG. 7 is a schematic side view of a third embodiment of an extension used in the electrode arrangement of FIG. 4, according to the invention.
Figure 8:
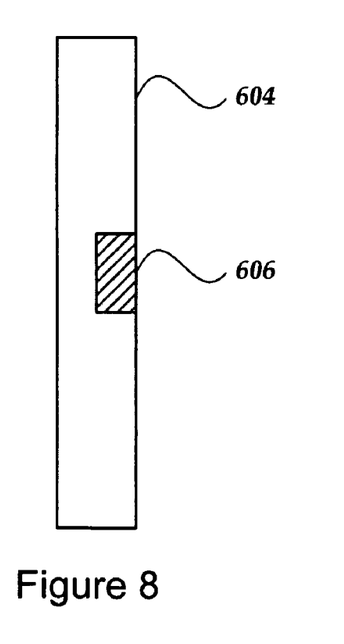
FIG. 8 is a schematic side view of a fourth embodiment of an extension used in the electrode arrangement of FIG. 4, according to the invention.
Figure 9:
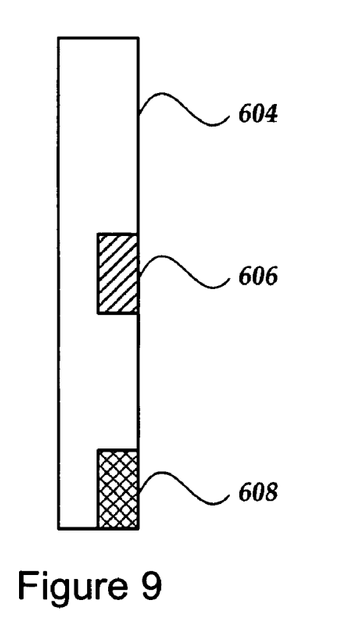
FIG. 9 is a schematic side view of a fifth embodiment of an extension used in the electrode arrangement of FIG. 4, according to the invention.

FIG. 4 illustrates another embodiment of an electrode arrangement 600. The electrode arrangement 600 includes a substrate 602 and one or more posts 604 extending from the substrate. The posts can include electrodes. Alternatively or additionally, strip electrodes, similar to those illustrated in FIG. 3, or any other type of electrode, can be disposed on the substrate 602.

The posts 604 can extend into the neurovascular bundle to position the electrodes even closer to the nerve fibers to be recruited. Optionally, these posts lie flat against the substrate (or in another pre-employment position) prior to and during implantation. Once in the body, the posts can be deployed. For example, the posts 604 can proceed to their full extension away from the substrate 602, as a result of an environmental stimulus such as the temperature of the body or the application of voltage to the electrodes or the like. Preferably, the posts are arranged so that as they are deployed into their final position they do not substantially damage tissue. In some embodiments, at least some of the posts may not fully extend due to the presence of intervening tissue.

There are a variety of methods for deploying the posts. For example, the posts can be formed of nitinol or another material that changes shape when heated (e.g., when heated to change phase.) The posts can be made of a material, such as a sponge-like material, that changes shape when hydrated. Piezoelectric devices can also be used to cause deployment of posts when an electrical signal is applied. In yet another embodiment, an infusion of a liquid (such as saline) can be provided through a central lumen to deploy the posts.

FIGS. 5-9 illustrate embodiments of posts 604 that include one or more electrodes 606, 608. In embodiments in which the extension includes two or more electrodes (e.g., FIGS. 7 and 9), the electrodes may be coupled together so that they are all either anodes or cathodes or some or all of the electrodes can be independently anodes or cathodes. The electrodes can be formed at a tip of the extension (see FIGS. 5, 7 and 9) or anywhere along the length of the extension (see FIGS. 6, 7, and 9.) The electrodes can take any form including rings around the extension (see FIGS. 6 and 7) or discrete structures, such as discs, squares, rectangles, etc. disposed on or imbedded in the extension (see FIGS. 8 and 9.)

The electrodes are formed of a conductive material. Preferably, the electrodes are formed of materials that do not substantially corrode under the operating conditions and in the operating environment for the expected lifetime of the stimulator device. Examples of suitable materials include metals, alloys, conductive plastics, and other conductive materials such as, for example, titanium, iridium, platinum, platinum iridium, stainless steel, and the like.

The electrodes can be formed entirely of a single conductive material, such as a metal or alloy, or one or both of the electrodes can be formed using a combination of conductive materials such as, for example, a conductive coating over a bulk metallic electrode. In other embodiments, one or both of the electrodes can be formed from a polymeric material that is at least partially, or fully, coated with a conductive coating, such as a metal, alloy, or conductive oxide (e.g., iridium oxide) coating.

The substrate can be formed using a plastic or cloth material with conductors disposed in or on the material to electrically couple the electrodes to the lead. The substrate should be biocompatible and not substantially degrade during the expected implantation period.

The electrode arrangement, or a lead connecting the electrode arrangement to a stimulation unit of stimulator device, can optionally include one or more lumens with corresponding opening(s) through which a drug can be infused to the nerve or adjacent tissue. The lumens can connect through the lead to the stimulator unit or a separate drug infusion unit that contains a reservoir of the drug and a pump that can provide the drug on a continuous, regular, irregular, or "as needed" basis. A processor may be provided to control the pump. The processor is optionally programmable from an external source by transmitting signals to the drug infusion processor. As an alternative, the lumen(s) can be accessed externally to infuse the drug using a drug infusion unit that is positioned on the skin of the patient or elsewhere or the lumen can be accessed to provide periodic infusions using a needle or the like.

Optionally, the electrode arrangement can also include one or more electrodes or sensors that are used to detect or measure the state of the nerve, the state of the erectile dysfunction or other disorder, or the state of the patient. These electrodes or sensors can be observed by the stimulator unit or a separate control unit.

Figure 10:
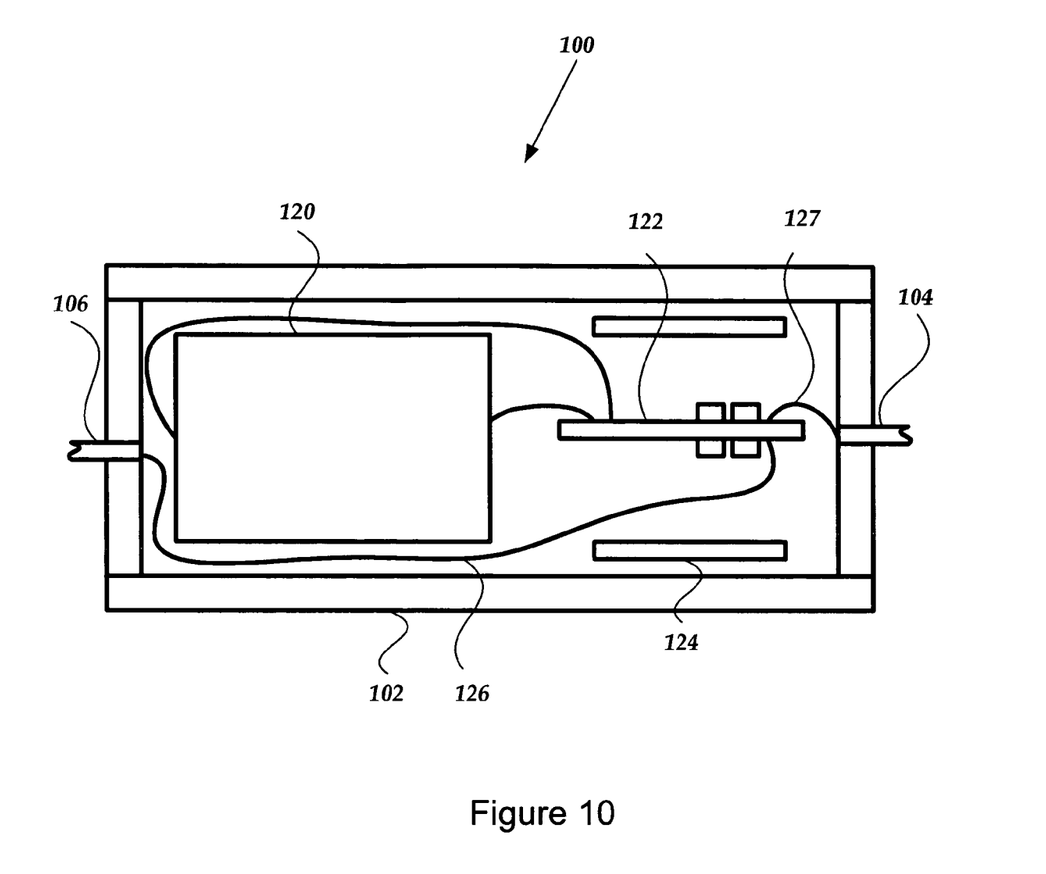
FIG. 10 is a schematic cross-sectional view of one embodiment of a stimulator unit, according to the invention.

An implantable stimulator device includes an implantable stimulator unit, an electrode arrangement that is disposed around or near the nerve, and a lead coupling the implantable stimulator unit to the electrodes on the cuff. FIG. 10 illustrates one embodiment of an implantable stimulator unit 100. The implantable stimulator unit 100 includes a housing 102, electrode conductors 104, 106 for connection to the lead, a power source 120, an electronics subassembly 122, and an optional antenna 124. Other embodiments of an implantable stimulator unit may include more or fewer components. It will be understood that the power source 120 and/or components of the electronics subassembly 122 and/or the optional antenna 124 can be provided outside of the housing in a separate unit and coupled to the implantable stimulator unit by a lead. The electronic subassembly 122 provides the electronics used to operate the stimulator device and generate the electrical pulses at the electrode arrangement to produce stimulation of the nerve.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A stimulator arrangement for a nerve in a body of a patient, comprising:
    an electrode arrangement having
        a substrate comprising an inner surface, the substrate comprising an arched portion and at least one relatively-flat stabilizing portion extending from, and abutting, each side of two opposing sides of the arched portion, wherein the inner surface of the arched portion is configured and arranged to receive the nerve upon implantation, wherein the arched portion is formed from a material configured and arranged to flatten the arched portion in response to exposure to the body after implantation such that the inner surface of the arched portion at least partially flattens the nerve, and
        a plurality of electrodes disposed on the inner surface of the substrate.

2. The stimulator arrangement of claim 1, further comprising a stimulator unit coupled to the electrodes of the electrode arrangement.

3. The stimulator arrangement of claim 1, wherein the electrode arrangement further comprises a plurality of posts that extend from the substrate and into tissue of the body.

4. The stimulator arrangement of claim 3, wherein at least a portion of the electrodes are disposed on the plurality of posts.

5. The stimulator arrangement of claim 4, wherein all of the electrodes are disposed on the plurality of posts.

6. The stimulator arrangement of claim 4, wherein the electrodes disposed on the plurality of posts are disposed at tips of the posts.

7. The stimulator arrangement of claim 4, wherein at least two electrodes are disposed on each of at least a portion of the plurality of posts.

8. The stimulator arrangement of claim 4, wherein at least a portion of the electrodes disposed on the plurality of posts are disposed as rings around the posts.

9. The stimulator arrangement of claim 4, wherein at least a portion of the electrodes disposed on the plurality of posts are disposed on only one side of the posts.

10. The stimulator arrangement of claim 3, wherein the plurality of posts are configured and arranged to lie next to the substrate prior to implantation and to extend away from the substrate after implantation.

11. A nerve stimulator, comprising:
    a stimulator unit;
    an electrode arrangement for disposition adjacent the nerve, wherein the electrode arrangement comprises
        a substrate comprising an inner surface, the substrate comprising an arched portion and at least one relatively-flat stabilizing portion extending from, and abutting, each side of two opposing sides of the arched portion, wherein the inner surface of the arched portion is configured and arranged to receive the nerve upon implantation, wherein the arched portion is formed from a material configured and arranged to flatten the arched portion in response to exposure to patient tissue after implantation such that the inner surface of the arched portion at least partially flattens the nerve, and
        a plurality of electrodes disposed on the inner surface of the substrate; and
    a lead coupling the stimulator unit to the electrodes of the electrode arrangement.

12. The nerve stimulator of claim 11, wherein the electrode arrangement further comprises a plurality of posts formed on the substrate.

13. The nerve stimulator of claim 12, wherein at least a portion of the electrodes are disposed on the plurality of posts.

14. The nerve stimulator of claim 11, wherein the nerve stimulator defines a lumen for providing a drug to tissue adjacent the electrode arrangement.

* * * * *

UNITED STATES PATENT AND TRADEMARK OFFICE
CERTIFICATE OF CORRECTION

PATENT NO. : 7,610,103 B2
APPLICATION NO. : 11/311502
DATED : October 27, 2009
INVENTOR(S) : Whitehurst et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 595 days.

Signed and Sealed this

Twelfth Day of October, 2010

David J. Kappos
*Director of the United States Patent and Trademark Office*